(12) United States Patent
Molkenthin

(10) Patent No.: US 11,389,105 B2
(45) Date of Patent: Jul. 19, 2022

(54) SYSTEMS AND METHODS FOR MEASURING A QUANTITY OF BREAST MILK CONSUMED BY A BABY

(71) Applicant: Brittany Molkenthin, Canterbury, CT (US)

(72) Inventor: Brittany Molkenthin, Canterbury, CT (US)

(*) Notice: Subject to any disclaimer, the term of this patent is extended or adjusted under 35 U.S.C. 154(b) by 320 days.

(21) Appl. No.: 16/174,792

(22) Filed: Oct. 30, 2018

(65) Prior Publication Data

US 2019/0125244 A1    May 2, 2019

Related U.S. Application Data

(60) Provisional application No. 62/579,499, filed on Oct. 31, 2017.

(51) Int. Cl.
*A61B 5/00* (2006.01)
*G01F 22/00* (2006.01)
(Continued)

(52) U.S. Cl.
CPC .......... *A61B 5/4238* (2013.01); *A61B 5/0022* (2013.01); *A61B 5/0064* (2013.01);
(Continued)

(58) Field of Classification Search
CPC ... A61B 5/4238; A61B 5/6805; A61B 5/0022; A61B 5/0064; A61B 5/6804;
(Continued)

(56) References Cited

U.S. PATENT DOCUMENTS 8,114,030 B2   2/2012  Ales et al.
8,280,493 B2  10/2012  Kolberg et al.
(Continued)

FOREIGN PATENT DOCUMENTS

BR   PI0815430 A2   2/2015
CN   107106022 A    8/2017
(Continued)

OTHER PUBLICATIONS

Gridneva, Z., et al., "Effect of Human Milk Appetite Hormones, Macronutrients, and Infant Characteristics on Gastric Emptying and Breastfeeding Patterns of Term Fully Breastfed Infants," Nutrients, vol. 9, Issue 15, pp. 1-21, Dec. 28, 2016.
(Continued)

*Primary Examiner* — Joseph M Santos Rodriguez
*Assistant Examiner* — Kaitlyn E Sebastian
(74) *Attorney, Agent, or Firm* — Murtha Cullina LLP; Anthony P. Gangemi

(57) ABSTRACT

The system includes at least one infrared light intensity sensor positioned on substrate to measure infrared light incident from a baby's stomach during a feeding. The infrared light is provided by an infrared light source. An initial intensity of infrared light incident from the human stomach is measured at the beginning of the feeding. A feeding intensity of infrared light incident from the human stomach is measured at the end of the feeding. The ratio of these infrared intensity measurements are used to calculate a value for the volume ingested into the human stomach during the feeding. The infrared light intensity measurements can be taken continuously to provide a real-time report of how the feeding is progressing, such as to a parent or doctor. The light source and sensor can be incorporated into an article of clothing to provide non-invasive measurements that do not physically obstruct the feeding.

24 Claims, 4 Drawing Sheets

(51) Int. Cl.
*A61B 5/0205* (2006.01)
*A61B 5/08* (2006.01)
*A61B 5/024* (2006.01)

(52) U.S. Cl.
CPC ........ *A61B 5/02055* (2013.01); *A61B 5/6804* (2013.01); *A61B 5/6805* (2013.01); *A61B 5/7275* (2013.01); *G01F 22/00* (2013.01); *A61B 5/024* (2013.01); *A61B 5/0816* (2013.01); *A61B 2503/04* (2013.01); *A61B 2560/0214* (2013.01)

(58) Field of Classification Search
CPC .............. A61B 5/02055; A61B 5/7275; A61B 2560/0214; A61B 5/0816; A61B 2503/04; A61B 5/024; G01F 22/00; G16H 40/67; G16H 50/30
See application file for complete search history.

(56) References Cited

U.S. PATENT DOCUMENTS

| | | |
|---|---|---|
| 11,064,924 B2 | 7/2021 | Woltjer et al. |
| 2007/0106112 A1 | 5/2007 | Gat et al. |
| 2008/0097169 A1* | 4/2008 | Long .................... A61B 5/4312 600/301 |
| 2010/0063771 A1* | 3/2010 | Miyata .................... G01N 21/77 702/156 |
| 2011/0190605 A1* | 8/2011 | Yamashita .......... A61B 5/02438 600/310 |
| 2014/0058199 A1 | 2/2014 | Glasel et al. |
| 2015/0223755 A1* | 8/2015 | Abir ..................... A61B 5/4288 600/300 |
| 2016/0183602 A1 | 6/2016 | Rider et al. |
| 2016/0256084 A1* | 9/2016 | Khoja .................. A61B 5/6838 |
| 2016/0287166 A1* | 10/2016 | Tran ....................... A61B 5/165 |
| 2016/0331298 A1 | 11/2016 | Burnett et al. |
| 2016/0367155 A1* | 12/2016 | Barrett ................. A61B 5/4848 |
| 2019/0242816 A1 | 8/2019 | Conner et al. |
| 2020/0384171 A1 | 12/2020 | Tian |

FOREIGN PATENT DOCUMENTS

| | | |
|---|---|---|
| RU | 2245679 C2 | 2/2005 |
| WO | 2005017641 A2 | 11/2005 |
| WO | 2019058284 A1 | 3/2019 |

OTHER PUBLICATIONS

Office Action dated Mar. 31, 2022, from the U.S. Patent and Trademark Office in U.S. Appl. No. 15/931,049.

* cited by examiner

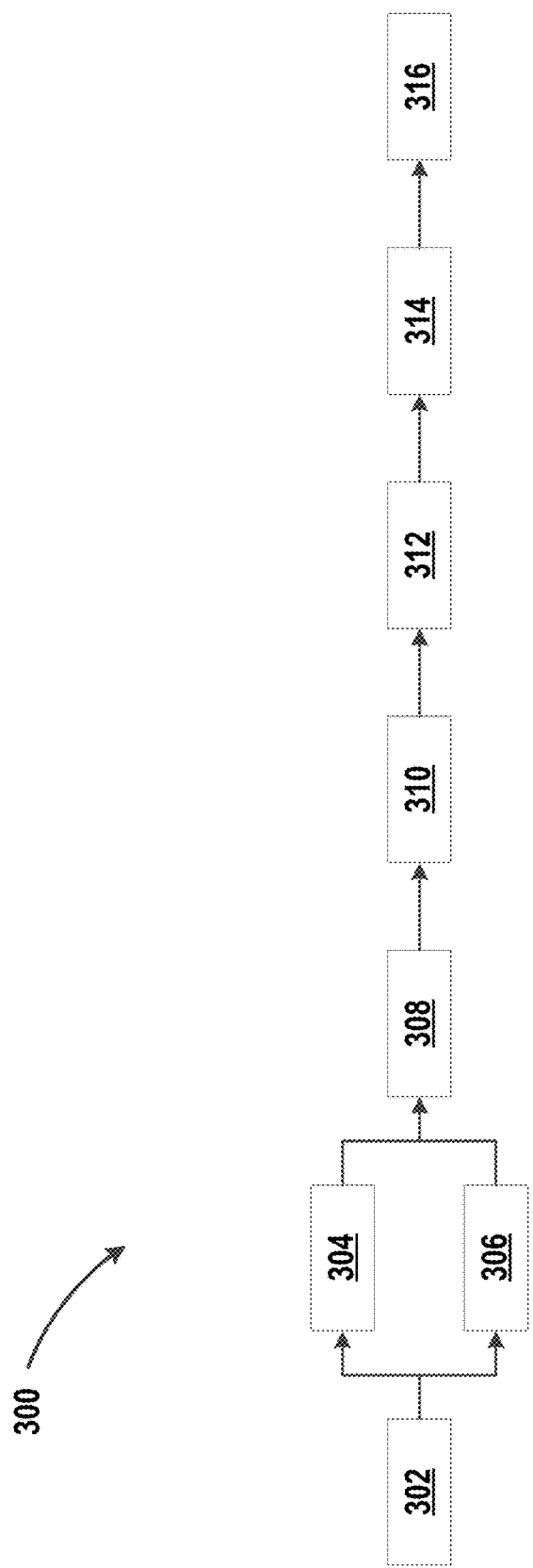

SYSTEMS AND METHODS FOR MEASURING A QUANTITY OF BREAST MILK CONSUMED BY A BABY

CROSS-REFERENCE TO RELATED APPLICATION

This application claims the benefit of U.S. Provisional Application Ser. No. 62/579,499, filed Oct. 31, 2017, which is incorporated herein by reference in its entirety, including any figures, tables, and drawings.

BACKGROUND

The number one barrier to breastfeeding is the question of, how does one know if the infant is receiving enough at feedings. According to the Surgeon General, nearly 50% of women stop breastfeeding within the first two weeks postpartum because of the apprehension of the amount of breast milk that the infant is receiving.

Studies have shown that there is a correlation between breastfeeding and the preventive measure it poses for infectious diseases. There is a substantial increase in hospitalization for infant's formula-fed versus infants that were breast-fed for respiratory tract infections. Through meta-analysis, sudden infant death syndrome has also shown to have a higher risk for infants formula-fed than those breast-fed. Breastfeeding has also shown to provide short-term protection against childhood obesity. Not only are there many benefits for the infant to be breast-fed, but also many for the mother. These benefits include decreased risk for premenopausal breast cancer, possible postmenopausal breast cancer, suppression of maternal infertility, rebalancing of postpartum hormonal changes, and possible protection of ovarian cancer.

Current systems give an estimate of breast milk intake with a large margin of error. Breast pumps, a large sector of the breastfeeding supplies market, also quantify the amount of breast milk that an infant can receive during feeding. Some disadvantages of breastfeeding pumps include that they interfere with the actual breastfeeding experience, and there is increased risk of contamination, bacteria, unsafe milk practices, and decreased benefits from the milk due to the freezing and thawing. There is also an increased risk of mastitis, nipple wounds, and trauma. The utilization of breast pumps does not decrease the risk of ovarian cancer, breast cancer, diabetes, and metabolic syndrome for the mother unlike the act of breastfeeding.

Some attempts have been made to solve the problem of calculating breast milk intake. One of the newest technologies on the market is Momsense® (Momsense Ltd., Ramat Gan, Israel). Momsense® claims to calculate sips to correlate intake via audio sounds. A sensor device is placed on the infant's jawline during feedings. A drawback of this technology is that research shows swallows alone only account for 50.8% of the variation of intake. This device also places wires on the infant's face, which is uncomfortable and disruptive for the feeding child. Another disadvantage is that infants often spit up, swallow air, or suck without actually feeding, and void during feeds.

Milksense™ is another device which claims, as it is placed on the mother's breast before, during and after feeding, to measure breast tissue resistance and correlate it to the amount of breast milk that is ingested during feedings. The disadvantages to this device are that it does not actually directly measure breast milk intake, the "let down" reflex may cause a margin of error, and there is a large variance of breast tissue amongst women.

Breast milk scales are another technological invention that aim to solve calculating how much breast milk was ingested during feedings. A baby is weighed before and after to correlate intake. However, the disadvantages of this solution include not directly measuring intake and infant voiding, spitting up, etc. during feedings which leads to more room for error.

SUMMARY

Some embodiments of the disclosed subject matter are directed to a system for quantifying a volume ingested by a human during a feeding. In some embodiments, the system includes a substrate, and at least one infrared light source positioned and at least one infrared light intensity sensor positioned on said substrate. In some embodiments, the light sensor is configured to detect intensities of infrared light incident from the human stomach. In some embodiments, the system includes a light intensity calculation module configured to identify an initial intensity of infrared light incident from the human stomach at a first instance, at least one feeding intensity of infrared light incident from the human stomach at a second instance, and the ratio of the at least one feeding intensity to the initial intensity. In some embodiments, a volume calculation module then outputs a value for the volume ingested into the human stomach between the first instance and the second instance that corresponds to the ratio of the at least one feeding intensity to the initial intensity.

Some embodiments of the present disclosure include a method for quantifying a volume ingested by a human during a feeding providing at least one infrared light source and at least one infrared light intensity sensor. In some embodiments, infrared light is emitted from at least one infrared light source to a human stomach. In some embodiments, an initial intensity of infrared light incident from the human stomach at the beginning of a feeding and a feeding intensity of infrared light incident from the human stomach at the end of the feeding are measured. In some embodiments, a volume ingested into the human stomach corresponds to the ratio of the feeding intensity to the initial intensity is calculated and displayed to a user, e.g., a parent, doctor, etc.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein:

FIG. 3 is a chart of a method of quantifying a volume ingested by a human during a feeding according to some embodiments of the present disclosure

DETAILED DESCRIPTION

It is recognized that certain limitations and features described in the present disclosure, such as light sources or light sensors, may need to be modified or removed in order to be in compliance with applicable local laws. By way of example, in the United States, certain limitations and features may need to be modified or removed in order to be in compliance with the Health Insurance Portability and Accountability Act (HIPAA).

Figure 1A:
FIG. 1A is a schematic drawing of a system for quantifying a volume ingested by a human during a feeding according to some embodiments of the present disclosure.

Referring now to FIG. 1A, some aspects of the disclosed subject matter are directed to a system 100 for quantifying a volume ingested by a human during a feeding. While the present disclosure shows and describes an exemplary embodiment of system 100 wherein the human is a baby and the volume ingested is breast milk, system 100 is not limited in this regard. As used herein, the term "feeding" is used to refer to the ingestion of milk or milk-like liquids and solids, e.g., breast milk.

In some embodiments, system 100 includes at least one substrate 110. The substrate includes one or more surfaces configured to comfortably interface with human skin. In some embodiments, at least one of the surfaces interfaces substantially uninterruptedly with a surface of the human skin. In some embodiments, substrate 110 includes a disk, spheroid body, polyhedral body, bib, shirt, blouse, dress, frock, onesie, or a combination thereof. In some embodiments, the substrate and/or the one or more substrate surfaces are composed of a biocompatible material. In some embodiments, the substrate is about 1 inch to about 2 inches in diameter. In some embodiments, the contact patch of the at least one of the surface with the surface of the skin is about 1 inch to about 2 inches.

In some embodiments, one or more infrared light sources 120 is positioned on substrate 110 and emit an amount of infrared light. The infrared light source 120 is configured to provide infrared light to the skin proximate a human stomach so that at least a portion of the light permeates the stomach lining and interacts with the stomach contents. The infrared light sources 120 can be of any number, layout, and/or orientation so long as light is delivered through the skin to the stomach in the manner described above. In some embodiments, one or more infrared light sources are arranged in a grid, a line, a circle, etc.

When in use, in some embodiments, substrate 110 is applied to the surface of the skin proximate the stomach, such that the surface of the skin and one or more surfaces of substrate 110 upon which infrared light sources 120 are disposed are abutting. In some embodiments, the infrared light from infrared light source 120 is emitted substantially perpendicular to the surface of the skin. In some embodiments, the infrared light from infrared light source 120 is emitted at an angle to the surface of the skin. In some embodiments, the infrared light from infrared light source 120 is emitted substantially perpendicular to the surface of substrate 110 on which infrared light source 120 is disposed. In some embodiments, the infrared light from infrared light source 120 is oriented at an angle to the surface of substrate 110 on which infrared light source 120 is disposed. In some embodiments, infrared light source 120 is one or more infrared LEDs. In some embodiments, infrared light source 120 emits light at a wavelength of about 900 nm to about 1000 nm. In some embodiments, infrared light source 120 emits light at a wavelength of about 940 nm. In some embodiments, the overall intensity of infrared light emitted by infrared light sources 120 is safe for prolonged use with humans, particularly babies. In some embodiments, the overall intensity of infrared light emitted by infrared light sources 120 is less than about 530 W/m$^2$.

In some embodiments, at least one infrared light intensity sensor 130 is positioned on substrate 110 and configured to detect intensities of infrared light incident from the human stomach. In some embodiments, infrared light intensity sensor 130 is configured to detect changes in infrared light intensity during the course of a feeding, as will be discussed in greater detail below. In some embodiments, infrared light intensity sensor 130 is a High Dynamic Range Digital light sensor. In some embodiments, infrared light intensity sensor 130 is an Adafruit® TSL light sensor. In some embodiments, infrared light intensity sensor 130 is a TSL2591 light sensor. In some embodiments, infrared light intensity sensor 130 is positioned on the same substrate 110 as infrared light source 120. In some embodiments, infrared light intensity sensor 130 is positioned on another substrate 110 from infrared light source 120. In some embodiments, infrared light intensity sensor 130 is positioned adjacent to infrared light source 120. In some embodiments, infrared light source 120 and infrared light intensity sensor 130 are positioned on substrate 110 such that each interface with the skin proximate the human stomach.

Figure 1B:
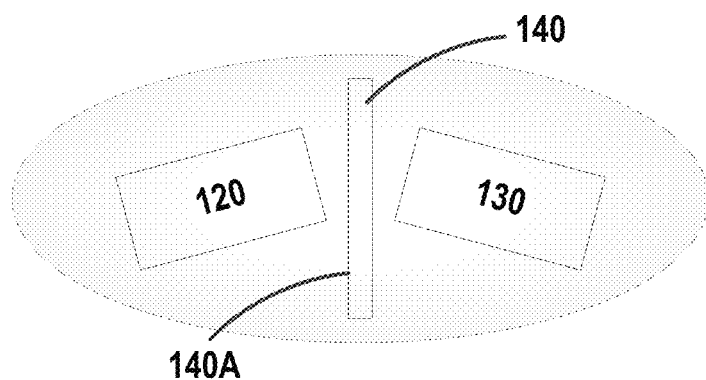
FIG. 1B is a schematic drawing of a system for quantifying a volume ingested by a human during a feeding according to some embodiments of the present disclosure.

Referring now to FIG. 1B, in some embodiments, system 100 includes a barrier 140 positioned to limit detection of infrared light directly from infrared light source 120 by infrared intensity sensor 130. In some embodiments, barrier 140 includes a reflective layer 140A. In some embodiments, system 100 includes one or more additional sensors including a heart rate sensor, a respiratory sensor, a temperature sensor, etc., or a combination thereof.

Figure 2:
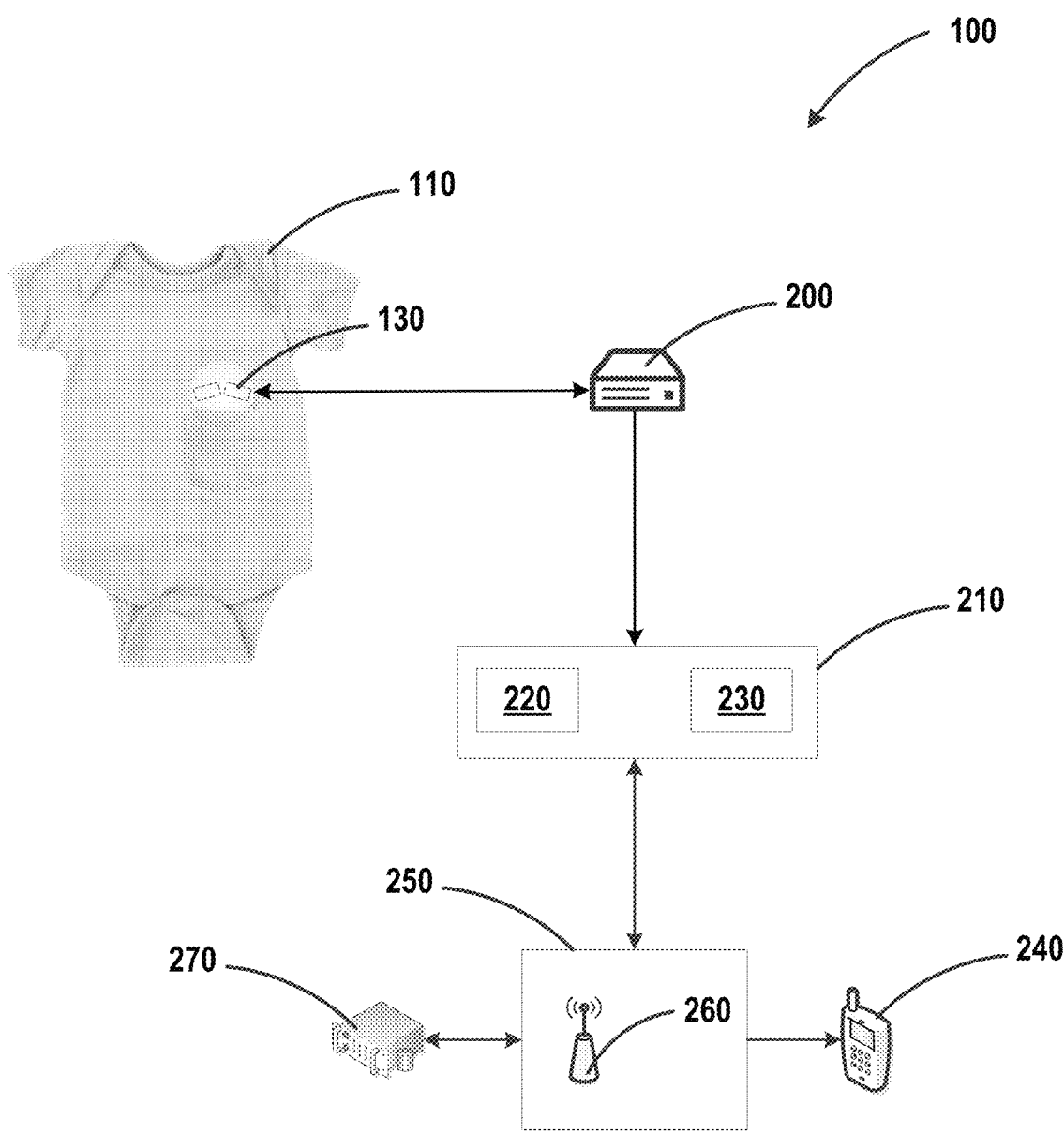
FIG. 2 is a schematic drawing of a system for quantifying a volume ingested by a human during a feeding according to some embodiments of the present disclosure.

Referring now to FIG. 2, system 100 includes a non-transitory computer storage medium 200 in communication with infrared light intensity sensor 130 and encoded with one or more computer programs 210 for outputting a volume ingested by a human. Non-transitory computer storage medium 200 includes one or more processing units and system memory. The non-transitory computer storage medium 200 is any suitable type of computer for executing one or more computer programs 210 to facilitate acquisition and analysis of light intensity data and export of ingested volume data, as is known to those having skill in the art.

In some embodiments, one or more computer programs 210 include a light intensity calculation module 220 configured to identify an initial intensity of infrared light incident from the human stomach. The initial intensity establishes a baseline value of infrared light incident from the stomach, a value that will change as the baby ingests milk during the course of the feeding. In some embodiments, the initial light intensity is measured at a first instance. In some embodiments, the feeding begins at a time t=0. In some embodiments, the first instance occurs t≤0. In some embodiments, the first instance occurs t=0. In some embodiments, the first instance occurs just after t=0. In some embodiments, light intensity calculation module 220 is configured to identify at least one feeding intensity of infrared light incident from the human stomach. In some embodiments, the feeding intensity is measured at a second instance. In some embodiments, a plurality of feeding intensities are measured during the course of a feeding. In some embodiments, the feeding stops at an endtime (t=E). In some embodiments, the second instance occurs at t≥0. In some embodiments, the second instance occurs at t≤E. In some embodiments, the second instance occurs just before t=E. In some embodiments, the second instance occurs at t=E. In some embodiments, light intensity calculation module 220 is configured to determine a ratio of the feeding intensity to the initial intensity. The ratio of the feeding intensity to the initial intensity is the measure of how the ingestion of a volume, i.e., e.g., the breast milk, is affecting the quantity of infrared light incident from the human stomach. In some embodiments, light intensity calculation module 220 calculates a plurality of these ratios corresponding to a plurality of feeding intensity measurements taken during a feeding. In some embodiments, feeding intensity measurements are taken continuously, as will be discussed in greater detail below. In some embodiments, the ratio of the feeding intensity to the initial intensity is calculated continuously.

In some embodiments, one or more computer programs 210 include a volume calculation module 230 configured to output a value for the volume ingested into the human stomach between the first instance and the second instance that corresponds to the ratio of the at least one feeding intensity to the initial intensity at the second instance, as will be discussed in greater detail below. In some embodiments, this volume value is calculated for each ratio of the feeding intensity to the initial intensity that is calculated. In some embodiments where the ratio of the feeding intensity to the initial intensity is calculated continuously, the volume value is also calculated continuously. In some embodiments, the volume value is output to a computer device 240 for display to a user, e.g., a doctor, nurse, parent, etc. In some embodiments, computer device 240 is a smart phone, tablet computer, desktop computer, personal digital assistant "PDA", and the like.

In some embodiments, system 100 includes a microcontroller system 250 providing power to and control over the infrared light intensity sensor 130 and infrared light source 120. In some embodiments, microcontrollers system 250 includes a data communication module 260 configured to enable communication of calculated light intensities and calculated volumes to the one or more databases from the light intensity calculation module and the volume calculation module. In some embodiments, microcontroller system 250 controls the intensity of infrared light source 120. In some embodiments, microcontroller 250 controls when infrared light source 120 is set to "ON," e.g., so that the light source need not be on during the entire duration of a feeding.

In some embodiments, system 100 includes one or more databases 270 including historical light intensity data from light intensity calculation module 220 and volume ingestion data from volume calculation module 230. The microcontroller system 250 can be any suitable controller setup suitable for powering and controlling infrared light intensity sensor 130 and infrared light source 120. In some embodiments, microcontroller system 250 is a Lilypad™ (Arduino, LLC, Somerville, Mass.). In some embodiments, microcontroller system 250 and non-transitory computer storage medium 200 are one and the same.

The volume ingested at a given instance during a feeding is correlated with the ratio of the feeding intensity to the initial intensity. In some embodiments, the correlation between the volume ingested and the light intensities measured by infrared light intensity sensor 130 is defined by the following Formula I:

$$V=(\log(I/I_o)+0.0036)/0.0007 \qquad \text{Formula I}$$

wherein $I_o$ is the initial intensity of infrared light incident from the human stomach and $I$ is the at least one feeding intensity of infrared light incident from the human stomach. In some embodiments, system 100 is calibrated for each individual human, e.g., each baby that uses the system. In some embodiments, the calibration is based on age, weight, waist size, etc., or combinations thereof. Formula I was determined experimentally as follows.

Example

The light source used was an infrared LED at 940 nm and the light sensor was an Adafruit® High Dynamic Range Digital Light Sensor TSL2591 (Adafruit Industries, New York, N.Y.). The source and receiver are placed adjacent to each other across the stomach of a phantom baby. The receiver was connected to a LilyPad™ having a power source, which returned the volume of milk in the infant stomach to the computer. Experiments were conducted as follows: the baby doll used was fitted with a clear plastic bag to represent the stomach of the phantom baby. The plastic bag was filled with 150 mL of water to simplify the contents of the human stomach. The plastic stomach region of the doll was covered by porcine skin to represent subcutaneous tissue. The sensor and LED source were placed adjacent to each other on top of the porcine skin. Using a funnel and a graduated cylinder, milk was poured into the infant simulating a sip of milk in increments of 2.5 mL starting at 0 mL to 60 mL of milk. The changes in infrared light intensity (I) were measured and transferred into a table. From the table, a graph was constructed of $\log(I/Io)$ on the y-axis and volume on the x-axis, with ($I_o$) representing the initial intensity of infrared light at 0 mL of milk. After multiple experiments, an average of intensity ratios was obtained for each volume of milk in mL (V). These values were used to construct a graph to obtain an equation relating volume and intensity correlation. Experimentation and collected results show a linear relationship between the ratio of infrared light intensity and volume of milk depicted in Formula I.

Some aspects of the present disclosure are directed to a method 300 for quantifying a volume ingested by a human during a feeding. At 302, at least one infrared light source and at least one infrared light intensity sensor are provided. At 304, the at least one infrared light source is positioned proximate a human stomach. At 306, the at least one infrared light intensity sensor is positioned to detect intensities of infrared light provided by the at least one infrared light source and incident from the human stomach. At 308, infrared light is emitted from the at least one infrared light source to a human stomach. In some embodiments, infrared light is emitted from the at least one infrared light source to the skin proximate the human stomach. In some embodiments, the infrared light is emitted at a wavelength of about 940 nm.

At 310, an initial intensity of infrared light incident from the human stomach is measured with the at least one infrared light intensity sensor at a first instance. In some embodiments, measured amount of infrared light is the sum total of all infrared light measured by one or more infrared light sensors. As discussed above, in some embodiments, the first instance is prior to, at, or near the beginning of a feeding. At 312, at least one feeding intensity of infrared light incident is measured from the human stomach with the at least one infrared light intensity sensor at a second instance. As discussed above, in some embodiments, the second instance is during, near the end, at the end, or after the end of feeding. In some embodiments, the feeding intensity of infrared light is calculated continuously. At 314, a volume ingested into the human stomach between the first instance and the second instance that corresponds to the ratio of the at least one feeding intensity to the initial intensity is calculated. In some embodiments, the volume ingested is calculated continuously. As discussed above, in some embodiments, the volume ingested is defined by Formula I. In some embodiments, at 316 the volume ingested is displayed to a user, e.g., via a computer device.

Methods and systems of the present disclosure advantageously provide an accurate system for measuring the actual volume of milk ingested by a baby during a breastfeeding session. The accuracy of the formula for converting measured infrared light intensities to volume provides the user with confidence in the data reported to the user. That the incident infrared light measured by the infrared light sensor is not affected by natural processes such as swallowing air, voiding during feedings, and spitting up that occur during feedings provides further confidence. The systems and methods are also truly non-invasive. There are no wires placed directly on the baby and there is no interference with the physical breastfeeding process, increasing comfort for both mom and baby. Finally, the systems and methods visualize the feeding in real-time, allowing parent to confirm whether or not a feeding is progressing successfully. Feeding data is also stored and tracked so that parents and other individuals, e.g., the baby's doctor, can view historical trends in the baby's feeding over time. The systems and methods of the present disclosure are particularly advantageous for premature babies, those born with complications, or those living in third world countries with limited resources.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A system for quantifying a volume ingested by a human during a feeding comprising:
    a substrate;
    at least one infrared light source positioned on said substrate and configured to provide infrared light to the contents of a human stomach;
    at least one infrared light intensity sensor positioned on said substrate and configured to detect intensities of infrared light incident from the human stomach; and
    a non-transitory computer storage medium in communication with said at least one infrared light intensity sensor and encoded with one or more computer programs for outputting a volume ingested by a human, the one or more computer programs including:
        a light intensity calculation module configured to identify an initial intensity of infrared light incident from the human stomach at a first instance, at least one feeding intensity of infrared light incident from the human stomach at a second instance, and the ratio of the at least one feeding intensity to the initial intensity; and
        a volume calculation module configured to output a value for the volume ingested into the human stomach between the first instance and the second instance, wherein the volume ingested is defined by a formula that correlates the ratio of the at least one feeding intensity to the initial intensity to the volume ingested.

2. The system according to claim 1, wherein the first instance is prior to a start of the feeding and the second instance is during the feeding.

3. The system according to claim 1, wherein the second instance is after the feeding is completed.

4. The system according to claim 1, the substrate includes a disk, spheroid body, polyhedral body, bib, shirt, blouse, dress, frock, onesie, or a combination thereof.

5. The system according to claim 1, further comprising a barrier positioned to limit detection of infrared light directly from the at least one infrared light source by the at least one infrared intensity sensor.

6. The system according to claim 5, wherein the barrier includes a reflective layer.

7. The system according to claim 1, wherein the at least one infrared light source is one or more infrared light emitting diodes.

8. The system according to claim 1, wherein the at least one infrared light source is positioned adjacent to the at least one infrared light intensity sensor such that each interface with the skin proximate the human stomach.

9. The system according to claim 1, wherein the infrared light is emitted at a wavelength of about 940 nm.

10. The system according to claim 1, wherein the volume ingested is defined by the following formula:

$$V=(\log(I/I_0)+0.0036)/0.0007$$

wherein $I_0$ is the initial intensity of infrared light incident from the human stomach and $I$ is the at least one feeding intensity of infrared light incident from the human stomach.

11. The system according to claim 1, further comprising one or more additional sensors including a heart rate sensor, a respiratory sensor, a temperature sensor, or a combination thereof.

12. A method for quantifying a volume ingested by a human during a feeding comprising:
    providing at least one infrared light source and at least one infrared light intensity sensor;
    emitting infrared light from the at least one infrared light source to the contents of a human stomach;
    measuring an initial intensity of infrared light incident from the human stomach with the at least one infrared light intensity sensor at a first instance prior to or at the beginning of a feeding;
    measuring at least one feeding intensity of infrared light incident from the human stomach with the at least one infrared light intensity sensor at a second instance during or after the feeding;
    calculating a volume ingested into the human stomach between the first instance and the second instance that corresponds to the ratio of the at least one feeding intensity to the initial intensity; and
    displaying the volume ingested to a user via a computer device.

13. The method according to claim 12, further comprising:
    positioning the at least one infrared light source to the skin proximate a human stomach;
    emitting infrared light from the at least one infrared light source to the contents of the human stomach; and
    positioning the at least one infrared light intensity sensor to detect intensities of infrared light provided by the at least one infrared light source and incident from the human stomach.

14. The method according to claim 12, wherein the infrared light is emitted at a wavelength of about 940 nm.

15. The method according to claim 12, wherein the volume ingested is defined by to the following formula:

$$V=(\log(I/I_0)+0.0036)/0.0007$$

wherein $I_0$ is the initial intensity of infrared light incident from the human stomach and $I$ is the at least one feeding intensity of infrared light incident from the human stomach.

16. The method according to claim 12, wherein calculating a volume ingested into the human stomach between the first instance and the second instance that corresponds to the ratio of the at least one feeding intensity to the initial intensity further comprises:
continuously calculating the volume ingested into the human stomach during a feeding.

17. A system for quantifying a volume ingested by a human during a feeding comprising:
a substrate;
at least one infrared light source positioned on said substrate and configured to provide infrared light to the contents of a human stomach;
at least one infrared light intensity sensor positioned adjacent to the at least one infrared light source and positioned to detect intensities of infrared light incident from the human stomach; and
a non-transitory computer storage medium in communication with said at least one infrared light intensity sensor and encoded with one or more computer programs for outputting a volume ingested by a human, the one or more computer programs including:
a light intensity calculation module configured to identify an initial intensity of infrared light incident from the human stomach at a first instance prior to or at the beginning of a feeding, a feeding intensity of infrared light incident from the human stomach at a plurality of additional instances during or after the feeding, and the ratio of the at least one feeding intensity to the initial intensity;
a volume calculation module configured to continuously output a value for the volume ingested during the feeding, wherein the volume ingested is defined by a formula that correlates the ratio of the latest feeding intensity of infrared light incident from the human stomach to the initial intensity to the volume ingested.

18. The system according to claim 17 wherein the substrate includes a disk, spheroid body, polyhedral body, bib, shirt, blouse, dress, frock, onesie, or a combination thereof.

19. The system according to claim 17, wherein the volume calculation module outputs a volume ingested according to the following formula:

$$V=(\log(I/I_0)+0.0036)/0.0007$$

wherein $I_0$ is the initial intensity of infrared light incident from the human stomach, $I$ is the feeding intensity of infrared light incident from the human stomach.

20. The system according to claim 17, further comprising:
one or more databases including historical light intensity data from the light intensity calculation module and volume ingestion data from the volume calculation module; and
a microcontroller system including a wireless data communication module configured to enable communication of calculated light intensities and calculated volumes to the one or more databases from the light intensity calculation module and the volume calculation module.

21. The system according to claim 1, wherein the volume ingested is defined by a formula defining a linear relationship between the ratio and the volume ingested.

22. The system according to claim 21, wherein the volume ingested is defined by a formula defining a linear relationship between the log of the ratio and the volume ingested.

23. The system according to claim 17, wherein the volume ingested is defined by a formula defining a linear relationship between the ratio and the volume ingested.

24. The system according to claim 23, wherein the volume ingested is defined by a formula defining a linear relationship between the log of the ratio and the volume ingested.

* * * * *